(12) United States Patent
DuPont, Jr. et al.

(10) Patent No.: US 10,675,820 B2
(45) Date of Patent: Jun. 9, 2020

(54) CONNECTOR AND TUBING ASSEMBLY AND METHOD OF MOLDING CONNECTOR AND TUBING ASSEMBLY

(71) Applicant: TBL Performance Plastics, LLC, Sparta, NJ (US)

(72) Inventors: Paul Robert DuPont, Jr., Sparta, NJ (US); Kevin McKiernan, Hillsborough, NJ (US)

(73) Assignee: TBL PERFORMANCE PLASTICS, LLC, Sparta, NJ (US)

( * ) Notice: Subject to any disclaimer, the term of this patent is extended or adjusted under 35 U.S.C. 154(b) by 404 days.

(21) Appl. No.: 15/864,725

(22) Filed: Jan. 8, 2018

(65) Prior Publication Data
US 2019/0009479 A1    Jan. 10, 2019

Related U.S. Application Data

(60) Provisional application No. 62/444,604, filed on Jan. 10, 2017.

(51) Int. Cl.
| | |
|---|---|
| *A61M 39/00* | (2006.01) |
| *B29C 65/00* | (2006.01) |
| *B29C 70/00* | (2006.01) |
| *F16L 47/00* | (2006.01) |
| *B29C 70/84* | (2006.01) |
| *A61M 39/08* | (2006.01) |
| *A61M 39/12* | (2006.01) |
| *B29C 65/70* | (2006.01) |
| *F16L 47/02* | (2006.01) |
| *F16L 47/32* | (2006.01) |

(Continued)

(52) U.S. Cl.
CPC .......... *B29C 70/845* (2013.01); *A61M 39/08* (2013.01); *A61M 39/12* (2013.01); *B29C 65/70* (2013.01); *B29C 66/1162* (2013.01); *B29C 66/5221* (2013.01); *B29C 66/52241* (2013.01); *B29C 66/7392* (2013.01); *F16L 47/02* (2013.01); *F16L 47/32* (2013.01); *A61M 2207/00* (2013.01); *B01D 46/0012* (2013.01); *B29L 2023/00* (2013.01); *B29L 2031/246* (2013.01); *F16L 41/021* (2013.01)

(58) Field of Classification Search
CPC ...... A61M 39/00; A61M 39/08; A61M 39/10; A61M 39/12; B29C 65/00; B29C 65/70; B29C 66/00; B29C 66/10; B29C 66/11; B29C 66/116; B29C 66/1162; B29C 66/50; B29C 66/52; B29C 66/522; B29C 66/5221; B29C 66/5224; B29C 66/52241; B29C 66/70; B29C 66/73; B29C 66/739; B29C 66/7392; B29C 70/00; B29C 70/80; B29C 70/84; B29C 70/845; F16L 47/00; F16L 47/02; F16L 47/30; F16L 47/32
See application file for complete search history.

(56) References Cited

U.S. PATENT DOCUMENTS

| | | | | |
|---|---|---|---|---|
| 9,192,753 | B2 * | 11/2015 | Lopez | A61M 39/10 |
| 9,278,206 | B2 * | 3/2016 | Fangrow | A61M 39/22 |
| 2013/0079730 | A1 * | 3/2013 | Mosler | A61M 39/10 |
| | | | | 604/244 |

* cited by examiner

*Primary Examiner* — Jacob T Minskey
*Assistant Examiner* — Matthew Hoover
(74) *Attorney, Agent, or Firm* — R. Neil Sudol; Henry D. Coleman

(57) ABSTRACT

An overmolding method for forming joints in a fluid-flow apparatus utilizes a connector or fitting as a component for mold forming. The connector or fitting is not removed after the overmolding and thus forms part of the joint assembly.

6 Claims, 12 Drawing Sheets

(51) Int. Cl.
*B29L 23/00* (2006.01)
*F16L 41/02* (2006.01)
*B01D 46/00* (2006.01)
*B29L 31/24* (2006.01)

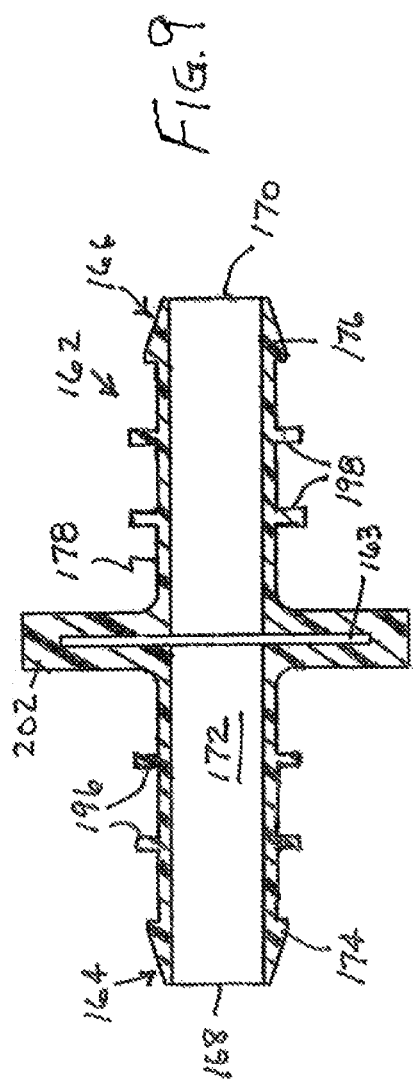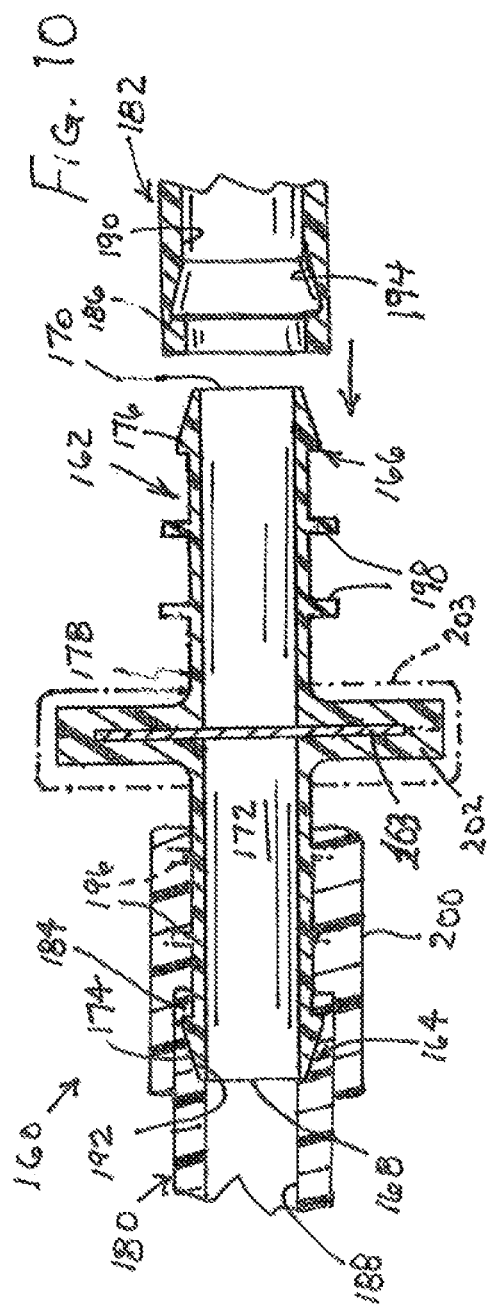

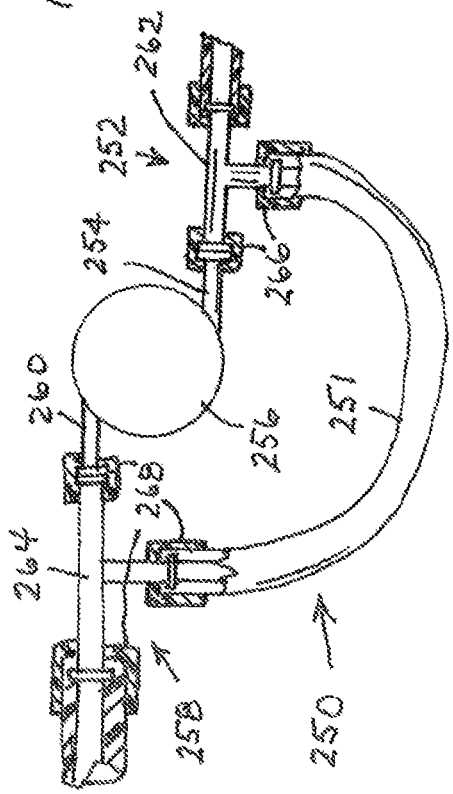
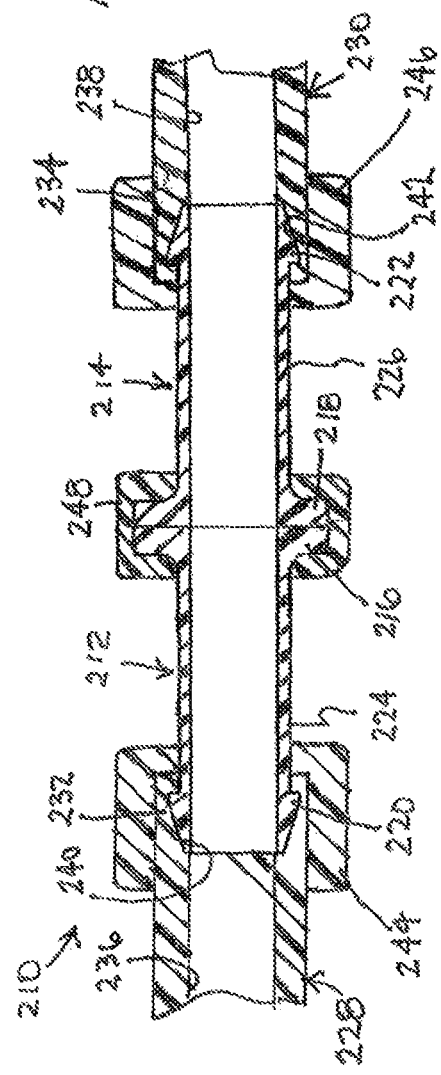

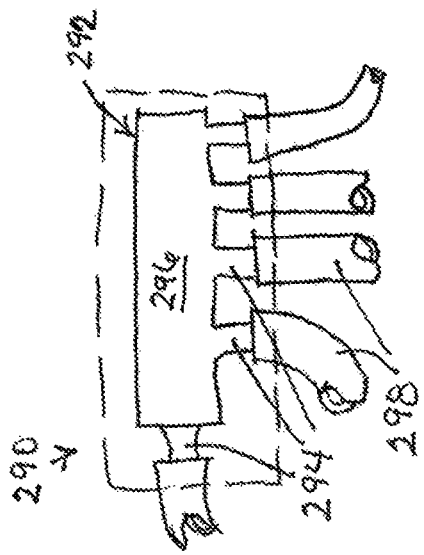
FIG. 14
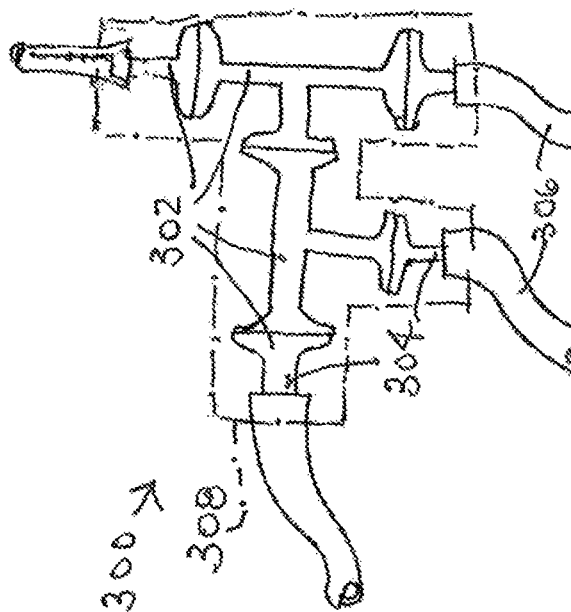
FIG. 15
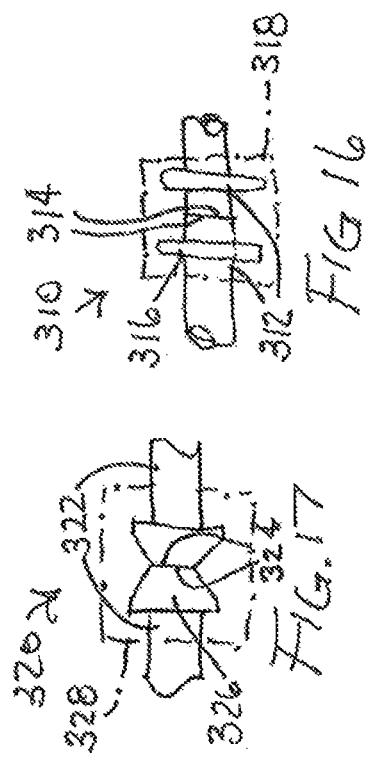
FIG. 16
FIG. 17

CONNECTOR AND TUBING ASSEMBLY AND METHOD OF MOLDING CONNECTOR AND TUBING ASSEMBLY

CROSS-REFERENCE TO RELATED APPLICATION

This application claims the benefit of U.S. Provisional Patent Application no. 62/444,604 filed Jan. 10, 2017, the entire disclosure of which is hereby incorporated by reference.

FIELD OF THE INVENTION

The invention relates to tubing systems used to transport fluidic materials in the manufacture, for instance, of pharmaceuticals and medicaments. This invention more particularly relates to methods of manufacturing such tubing systems and particularly connection or joint assemblies thereof.

BACKGROUND OF THE INVENTION

For as long as drug products have been manufactured, the Biotech and Pharmaceutical industry used various methods to convey liquid products during the drug manufacturing process. In more recent years the industry's mindset has been to move away from traditional processes which relied on fixed capital intensive piping systems. Traditional systems are typically made from stainless steel or glass lined piping. Because these systems were capital intensive, drug manufacturers would go to large expense to validate cleanability and ensure no cross contamination from one batch to the next. Facility owners have had to invest in expensive large and sophisticated utility plants with chemical dosing systems and ultra-high purity steam systems necessary to sterilize the systems.

More recently manufacturing methods have trended to faster drug development and faster regulatory clearance to market. This trend is in conjunction with, and partially due to, world health authorities granting fast track approvals of vaccines and therapies to combat the new strains of mutated diseases, which we are seeing more frequently.

Today, many of the new drug manufacturing processes utilize "Single Use Systems". These are basically pre-sterilized sub-systems manufactured from plastics. They are used once, or a limited number of times, and then discarded. For example, instead of a stainless steel vessel and piping, a typical single use system would consist of a number of plastic bag(s) connected by a series of plastic tubing sets with mechanical connection means, including tubing manifolds, between bags, tubes and other system components. Concern over the seal integrity on tubing manifolds is of paramount concern.

There are many ways a tube-to-tube connection or multi-lumen tube connection can be made. For less critical applications, methods can be as simple as a nylon cable tie or stainless crimp ring over a hose end that has a barbed fitting inserted ("tube to hose barb" connection) but for the most critical applications this type of connection may present too much risk to seal integrity. For this reason, molded, integrally molded, or overmolded, connections between tube ends are desired, and have become recognized, as a better alternative.

Here we do not mean already-molded connectors attached to tubes by mechanical means such as threading, banding, crimping, etc. Instead we refer to methods of injecting plastic around tube ends in a mold to form a molded connector that becomes attached to the tubes during the molding process. Prior art includes designs and methods to accomplish this. There are many drawbacks to the existing methods, which rely on several invasive steps in the manufacturing process, presenting high risk of potentially contaminating or damaging the interiors of the tubes. In addition, current methods are limited in the interior shape of the flow path because of the necessity of removing the temporary inserts around which the flow path is molded.

Current practice by multiple industry participants is overmolding silicone (thermoset material) around silicone tubes with temporary mold inserts. Then the silicone is cured and the inserts are removed, often by breaking them first. Multiple patents exist which describe and claim the process.

SUMMARY OF THE INVENTION

The present invention is directed to a method and device design that uses a molding operation to fasten a plurality of tubes to one or more fittings. The material deposited in the molding operation does not form the flow path. Instead, the flow path is formed by assembly, in a preferred embodiment, of two or more tubes to a single fitting, adapter, or connector piece. A combination of component materials, component geometries, mold cavity design, molding material, and molding parameters, such as time and temperature, causes the tubes to become securely connected, and fused, to the connector piece, with fluid-tight seals and with a relatively smooth transition between the inner diameters of the connector and tubes.

In comparison to current industry methods, this invention eliminates the need for inner molding pieces and passage-forming assemblies of the prior art, which are temporary inserts removed after the overmolding process. In omitting such inner molding pieces and passage-forming assemblies the present invention eliminates the potential for contamination and wall damage inside the fluid path. The present method allows for a fitting or adapter, tubes and molding material to all be different materials. In the preferred embodiment, the molding material is a thermoplastic that solidifies by cooling without need of a curing step. The connector piece provides strength and resistance against the pressure of the molding operation. The respective geometries of the connector piece and tubes provide a seal against molding material entering the pre-established fluid path.

The invention has the added benefit that, because no inner molding pieces need to be removed, the inner cavity of the connector piece can be larger in cross-section than, and of different shape from, the tube inner passages. This may be the case, for example, when the connector piece is made as an assembly of multiple components.

In accordance with the present invention, a method of molding a connector and tubing assembly comprises providing a connector member (or fitting or adapter, optionally including a functional insert such as a filter element) including a plurality of ends with respective openings that communicate with one another via a lumen of the connector member. The connector member has one or more projections extending outwardly from an outer surface. The one or more projections are typically spaced from the ends of the connector member but may be alternatively located at the ends. At least one of the ends of the connector member is inserted into a terminal portion of a respective tube. Then a layer of thermoplastic or polymeric material is molded about at least a portion of the connector member and about the terminal portions of the tube. During the molding process, the thermoplastic or polymeric material melts at least a portion of the one or more projections into the thermoplastic or polymeric layer, so that the material of the projections is incorporated into and is irrevocably bonded to the thermoplastic or polymeric material.

The molding of the thermoplastic or polymeric material about the connector member and the one ore more tubes bonds the tubes to the connector member and forms a fluid tight seal between the tubes and the connector member. The preferably partial melting of the one or more projections on the connector member into the thermoplastic/polymeric material strengthens and reinforces the coupling of the connector member to the tube(s).

In accordance with another embodiment of the present invention, a method of molding a connector and tubing assembly utilizes a connector member (fitting, adapter, joint insert) including a plurality of ends with respective openings that communicate with one another through a lumen of the connector member. The connector member is formed at at lest one of the ends with a projecting structure (such as a ridge, barb, lug, rib, or tooth) extending outwardly from an outer surface of the connector member. The method also utilizes at least one tube having a terminal portion with a profiled inner surface with a recess configured to receive or seat the projecting structure. Preferably, but not necessarily, the recesses are of substantially the same size and shape as the respective projecting structures. The method comprises inserting the at least one end of the connector member into the terminal portion of the at least one tube so that the projecting structure is received or seated in the recess. Subsequently one molds a layer of thermoplastic or polymeric material about the connector member and about the terminal portion of the tube so that the thermoplastic or polymeric layer is bonded to the connector member and the tube's terminal portion.

The seating of projecting structures of the connector member in geometrically identical (optionally slightly larger) recesses in the inner surfaces of the tubes also serves to strengthen and reinforce the coupling of the connector member to the tubes. In addition, this mating of the connectors' projecting structures and the tubes' recesses can allow better continuity or smooth transition of the inner-diameter lumen surfaces of the connector member and the tubes.

In accordance with a further embodiment of the present invention, a method of molding a connector and tubing assembly comprising providing a plurality of connector members each including a plurality of ends with respective openings that communicate with one another through a lumen of the respective connector member. The connector members are formed with respective projecting structures extending radially outwardly from an outer surface of the respective connector member. The method further comprises placing one end of each of the connector members in juxtaposition with an end of another one of the connector members so that the connector members communicate with one another and are in direct or indirect contact or engagement with one another at the contacting ends of the connector members. ("Indirect contact" means, for instance, that a sealing ring or gasket is placed between the juxtaposed ends of the connector members.) Typically, one ore more ends of the connector members different from the contacting ends are inserted into terminal portions of respective tubes. Subsequently a layer of thermoplastic or polymeric material is molded about at least a portion of each of the connector members including the juxaposed ends and the projecting structures and about the terminal portions, if any, so that the thermoplastic or polymeric material is bonded to the connector members at least in a regiona about the juxtaposed ends and so that the thermoplastic or polymeric layer fixes the connector members to one another. The juxtaposed ends of the connector portions are maintained in juxtaposition with one another during the molding of the thermoplastic or polymeric material.

Pursuant to this embodiment of the invention, the connector members may be tapered with larger ends having the projecting structures engaging another connector member and the smaller ends inserted into the respective tubes. This facilitates certain flow patterns during the manufacture of medicaments. For instance, the cross-sectional area of a junction of two or more incoming tubes may be larger than the cross-sectional area of either of the inflow passages, for accommodating the combined flow rates, while an exit conduit may be smaller to increase fluid flow rate. Multiple junctions of larger diameter alternating with tubes of smaller diameter may be formed exemplarily to increase turbulence and thus enhanced mixing at desired locations.

In accordance with a yet another embodiment of the present invention, a method of molding a connector and tubing assembly utilizes a plurality of connector members and a plurality of tubes. The connector members each include a plurality of ends with respective openings that communicate with one another through a lumen of the respective connector member. The method comprises placing the connector members and the tubes in a circuit, wherein the connector members and the tubes communicate with one another and are in contact or engagement with one another, wherein ends of the connector members are inserted into respective terminal portions of respective ones of the tubes, and wherein at least one of the connector members has an end inserted into one of the tubes, where that one tube is closed or inaccessible from an end opposite the one connector member. One subsequently molds a layer of thermoplastic or polymeric material about the connector members and about the terminal portions so that the thermoplastic or polymeric material is bonded to the connector members and the terminal portions and so that the thermoplastic or polymeric layer fixes the connector members to one another and to the tubes. A joint or coupling of the thermoplastic material is thus formed between the one connector member and the one tube, even though the one connector member is not accessible via the one tube.

A resulting fluid-flow circuit may exemplarily include an active circuit component such as a pump or mixer. A feedback loop, shunting some of the output of the active circuit element back to an input side thereof, may be constructed by the foregoing method.

Pursuant to a feature of the present invention, with application to any of the above described method embodiments, the molding of the layer of thermoplastic or polymeric material about at least of portion of a connector member and about respective terminal portions of tubes coupled to that connector member includes applying the thermoplastic or polymeric material in separate aliquots at the terminal portions to form a plurality of spaced overmolded sleeves. The over-molded sleeves may be equal in number to the terminal ends, but that is not necessarily the case, for instance, where multiple connector members are molded directly to one another.

Concomitantly, a connector and tubing assembly comprises, pursuant to the present invention, (i) a connector member including a plurality of ends with respective openings that communicate with one another via a lumen of the connector member, (ii) at least one tube, one of the ends being of the connector member being disposed in a terminal portion of the at least one tube, and (iii) a molded layer of thermoplastic or polymeric material disposed about at least a portion of the connector member and the terminal portion of the at least one tube. The connector member has one or more projections extending outwardly from an outer surface of the connector member. The one or more projections are each at least partially melted and integrated into the thermoplastic or polymeric material, thereby enhancing bonding of the connector member to the layer of thermoplastic or polymeric material.

Another related connector and tubing assembly comprises, pursuant to the present invention, a connector member having a plurality of ends with respective openings that communicate with one another through a lumen of the connector member. The connector member is formed at at least one of the ends with a projecting structure extending radially outwardly from an outer surface of the connector member. The connector and tubing assembly further comprises at least one tube that has a terminal portion with a profiled inner surface having a recess configured to receive or seat the projecting structure. The at least one end of the connector member with the projecting structure is inserted into the terminal portion of the at least one tube so that the projecting structure is received or seated in the recess. A thermoplastic or polymeric layer is provided (molded) about at least a portion of the connector member and about the terminal portions of the tubes so that the thermoplastic or polymeric layer is bonded to the connector member and the tube terminal portion. The recess seating the projecting structure may be geometrically congruent to, that is, of substantially the same size (optionally and not necessarily slightly larger) and shape as, the respective projecting structure.

A further connector and tubing assembly comprises, pursuant to the present invention, a plurality of tubes and a plurality of connector members. Each connector member includes a plurality of ends with respective openings that communicate with one another through a lumen of the respective connector member. The connector members are each formed with a projecting structure extending radially outwardly from an outer surface of the respective connector member. One end of each of the connector members is disposed in juxtaposition with an end of another one of the connector members so that the connector members communicate with one another and are in direct or indirect contact or engagement with one another at the juxtaposed ends of the connector-members. Ends of the connector members different from the contacting ends are optionally disposed in respective terminal portions of respective ones of the tubes. A thermoplastic or polymeric layer is molded about at least a portion of each of the connector members at least in a region about the juxtaposed ends of the connector members, so that the thermoplastic or polymeric layer is bonded to the connector members and fixes the connector members to one another with the juxtaposed ends of the connector portions in direct or indirect engagement with one another. Each of the projecting structures may be a flange, optionally an annular flange, or one or more tongues or nubs.

Yet another connector and tubing assembly comprises, pursuant to the present invention, a plurality of connector members and a plurality of tubes. The connector members each include a plurality of ends with respective openings that communicate with one another through a lumen of the respective connector member. The connector members and the tubes are disposed in a circuit having at least one nonlinear path segment. The connector members and the tubes communicate with one another and are in contact or engagement with one another, ends of the connector members being disposed in respective terminal portions of respective ones of the tubes. A thermoplastic or polymeric layer is provided or molded about at least a portion of each of the connector members and about the terminal portions so that the thermoplastic or polymeric layer is bonded to the connector members and the terminal portions and so that the connector members are fixed to one another and to the tubes by the molded thermoplastic or polymeric layer.

In any of the above-described embodiments of a connector and tubing assembly in accordance with the present invention, the layer of thermoplastic or polymeric material may be provided only about respective terminal portions of tubes coupled to that connector member, and about contacting ends of multiple connector members, so that the assembly includes a plurality of spaced over-molded sleeves.

BRIEF DESCRIPTION OF THE DRAWINGS

FIG. 9 is a cross-sectional view of an inline filter component for a fluid-flow circuit assembly made by a manufacturing method pursuant to the present invention.

FIG. 10 is a cross-sectional view of a connector and tubing assembly or fluid-flow circuit arrangement pursuant to the present invention, incorporating the inline filter of FIG. 9 and constructed by the method of the present invention.

FIG. 11 is a cross-sectional view of yet another connector and tubing assembly or fluid-flow circuit joint in accordance with the present invention fabricated by a method in accordance with the invention.

FIG. 12 is partially a cross-sectional view and partially a side elevational view of a fluid-flow circuit, in accordance with the present invention, incorporating connector and tubing assemblies or fluid-flow circuit joints fabricated by a method in accordance with the invention.

FIG. 14 is a schematic diagram of a first additional connector and tubing assembly or fluid-flow circuit joint in accordance with the present invention fabricated by a method in accordance with the invention.

FIG. 15 is a schematic diagram of a second additional connector and tubing assembly or fluid-flow circuit joint in accordance with the present invention fabricated by a method in accordance with the invention.

FIG. 16 is a schematic diagram of a third additional connector and tubing assembly or fluid-flow circuit joint in accordance with the present invention fabricated by a method in accordance with the invention.

FIG. 17 is a schematic diagram of a fourth additional connector and tubing assembly or fluid-flow circuit joint in accordance with the present invention fabricated by a method in accordance with the invention.

DETAILED DESCRIPTION

Figure 1:
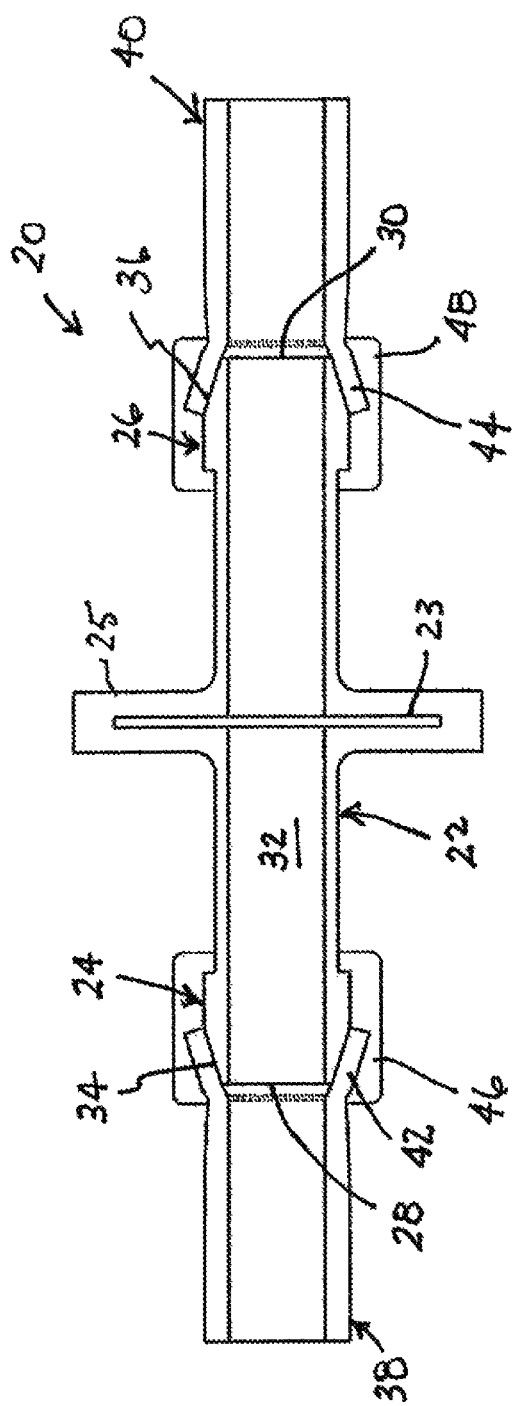
FIG. 1 is a cross-sectional view of a connector and tubing assembly or fluid-flow circuit assembly in accordance with the present invention fabricated by a method in accordance with the invention, where a connector member incorporates a filter element and accordingly functions as an inline filter.
Figure 2:
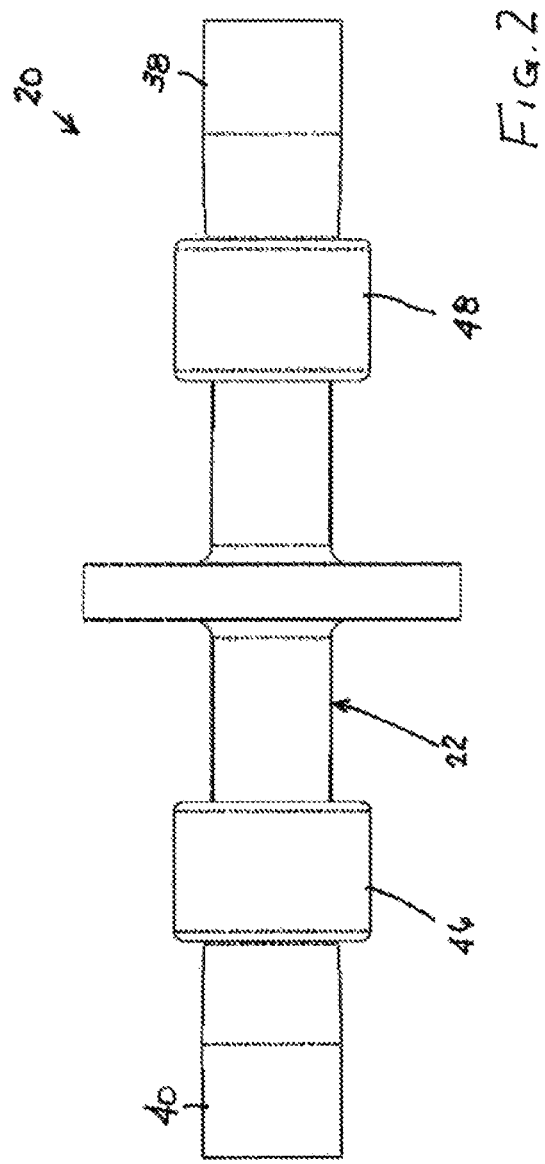
FIG. 2 is a side elevational view of the connector and tubing assembly of FIG. 1.

As depicted in FIGS. 1 and 2, a connector and tubing assembly 20 comprises a preformed connector member or fitting element 22 incorporating a filter element 23 within a flange 25 and having a pair of ends 24 and 26 with respective openings 28 and 30 that communicate with one another through a lumen 32 of the connector member. Connector or inline filter member 22 is formed at each of end 24 and 26 with a respective tapered or conical structure 34 and 36 extending radially outwardly from an outer surface 37 of the connector member. Two tubes 38 and 40, which are equal in number to the ends 24 and 26 of the connector member 22, each have a terminal portion 42 and 44. Ends 24 and 26 of connector member 22 are each inserted into the terminal portion 42 and 44 of a respective tube 38 and 40 so that the respective terminal portion is deformed to flare outwardly, as shown in FIG. 1. A layer of thermoplastic or polymeric material is molded in separate amounts or aliquots at respective locations about at least a portion of connector member 22 and about the terminal portions 42 and 44 of tubes 38 and 40 so that the layer of thermoplastic or polymeric material is bonded to the connector member and the terminal tube portions to forma plurality of spaced sleeves or joint knuckles 46 and 48.

Connector and tubing assembly 20 is fabricated by inserting each of the ends 24 and 26 into a respective terminal portion 42 and 44 of tubes 38 and 40 so that the respective terminal portion 42, 44 is deformed to flare outwardly. Subsequently the thermoplastic or polymeric material is molded about at least a portion of connector member 22 and about terminal portions 42 and 44 so that the thermoplastic or polymeric material is bonded to the connector member and the terminal portions. Where the thermoplastic material is applied in spaced batches or aliquots, spaced thermoplastic sleeves or knuckles are formed. It is to be noted that the thermoplastic material may be applied as a single continuous overlayer over the entire connector member 22. (See FIGS. 5 and 6.)

Figure 3:
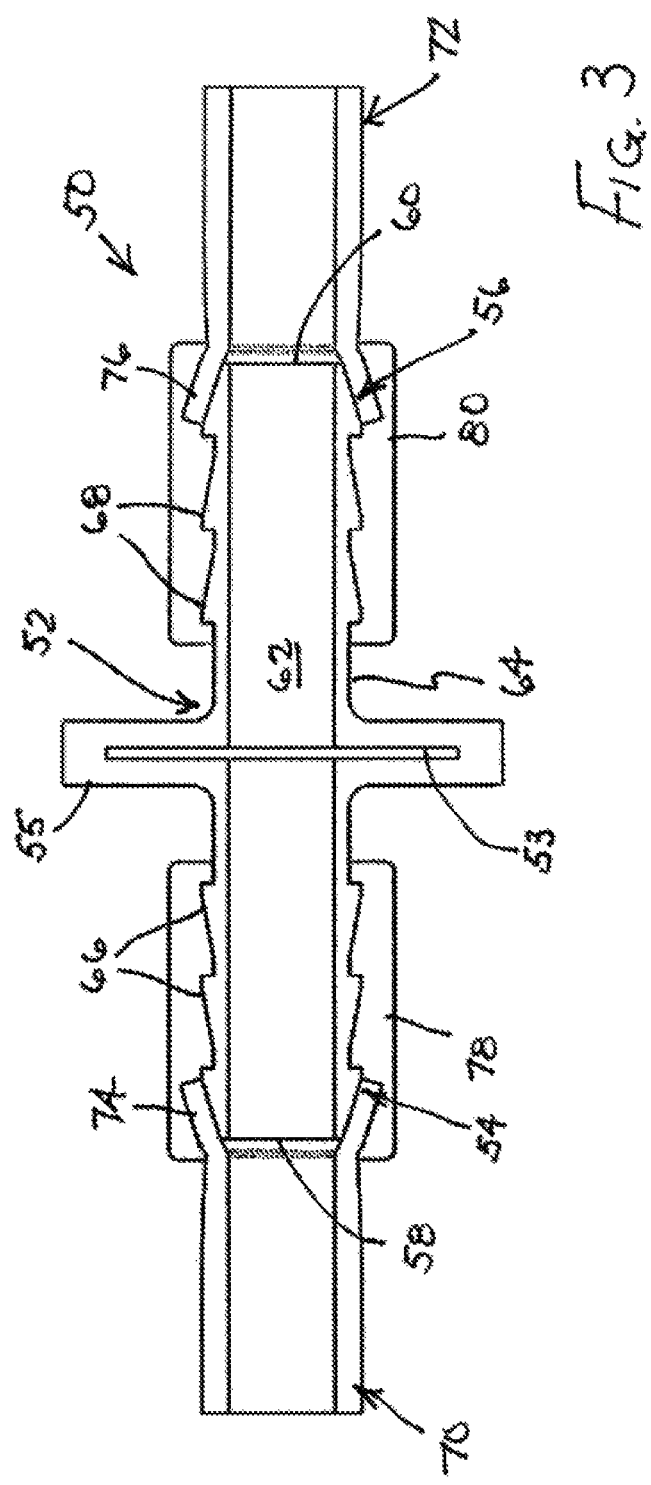
FIG. 3 is a cross-sectional view of another connector and tubing assembly or fluid-flow circuit construction in accordance with the present invention fabricated by a method in accordance with the invention, where a connector member or fitting incorporates a filter element and accordingly serves as an inline filter.
Figure 4:
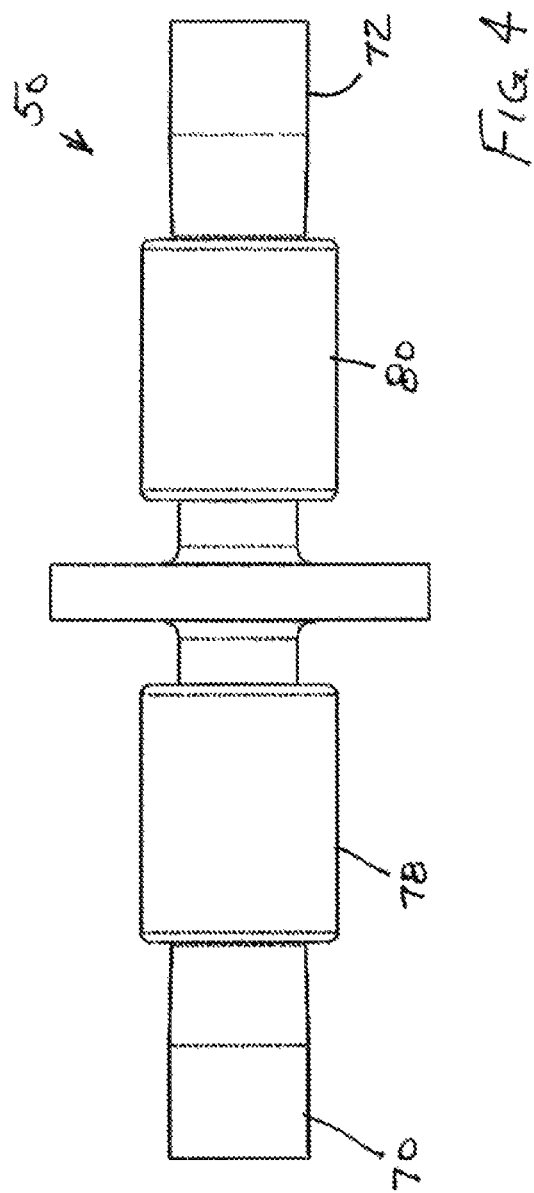
FIG. 4 is a side elevational view of the connector and tubing assembly of FIG. 3.

As shown in FIGS. 3 and 4, a connector and tubing assembly 50 comprises a preformed connector member or fitting 52 incorporating a filter element 53 within a flange 55 and having a pair of ends 54 and 56 with respective openings 58 and 60 that communicate with one another through a lumen 62 of the connector member. The connector or inline filter member 62 is formed along an outer surface 64 with two sets of tapered annular ridges or conical projections 66 and 68, each set including a member at a respective end 54 and 56 of the connector or joint fitting element 52. Two tubes 70 and 72 equal in number to the ends 54 and 56 of the connector member 52 each have a terminal portion 74 and 76. Ends 54 and 56 of connector member 52 are each inserted into the terminal portion 74 and 76 of a respective tube 70 and 72 so that the respective terminal portion is deformed to flare outwardly, as shown in FIG. 3. A layer of thermoplastic or polymeric material is molded in separate amounts or aliquots at respective locations about at least a portion of connector member 52 and about the terminal portions 74 and 76 of tubes 70 and 72 so that the layer of thermoplastic or polymeric material is bonded to the connector member and the terminal tube portions to form a plurality of spaced sleeves or joint knuckles 78 and 80 that respectively cover or envelop the tapered annular ridges or conical projections 66 and 68.

Connector and tubing assembly 50 is fabricated by inserting each of the ends 54 and 56 into a respective terminal portion 74 and 76 of tubes 70 and 72 so that the respective terminal portion 74, 76 is deformed to flare outwardly. Subsequently molding the thermoplastic or polymeric material is molded about at least a portion of connector member 52 and about terminal portions 74 and 76 so that the thermoplastic or polymeric material is bonded to the connector member and the terminal portions. As shown in FIGS. 3 and 4 the thermoplastic material is applied in spaced batches or aliquots to for separate sleeves 78 and 80. Alternatively the thermoplastic material may be applied as a single continuous overlayer over the entire connector member 52. (See FIGS. 5 and 6.)

Figure 5:
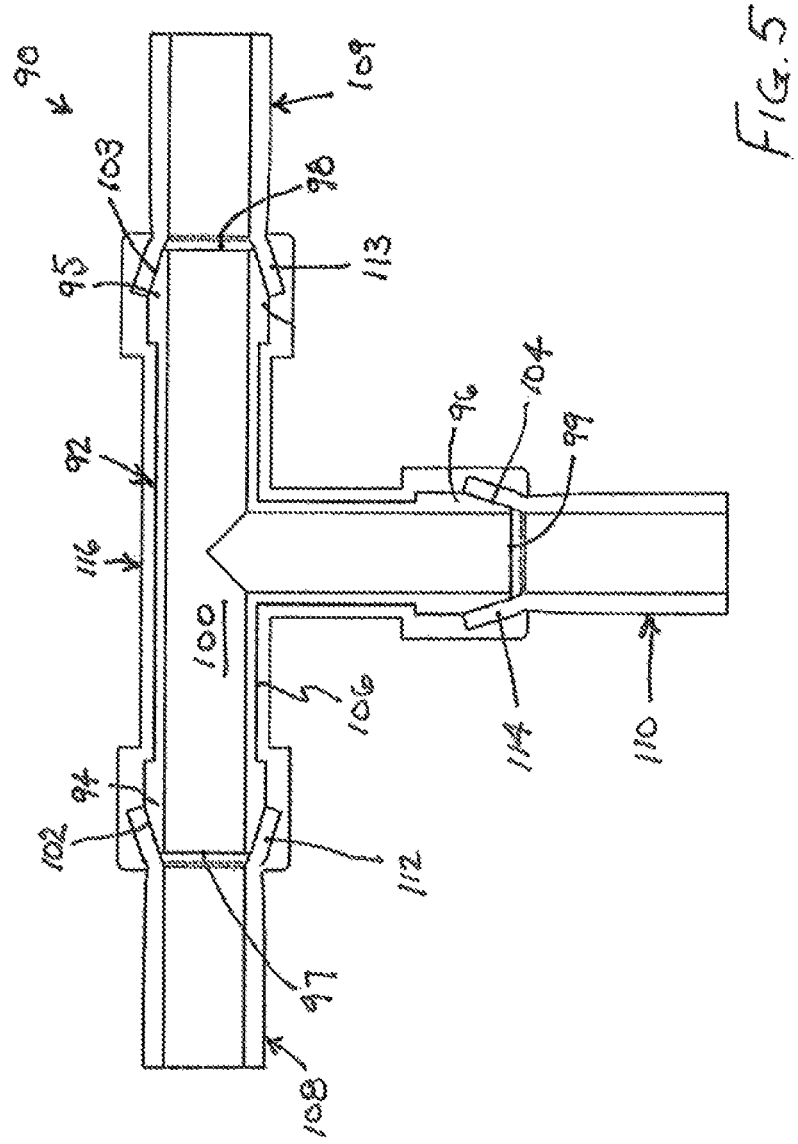
FIG. 5 is a cross-sectional view of a further connector and tubing assembly or fluid-flow circuit joint in accordance with the present invention fabricated by a method in accordance with the invention.
Figure 6:
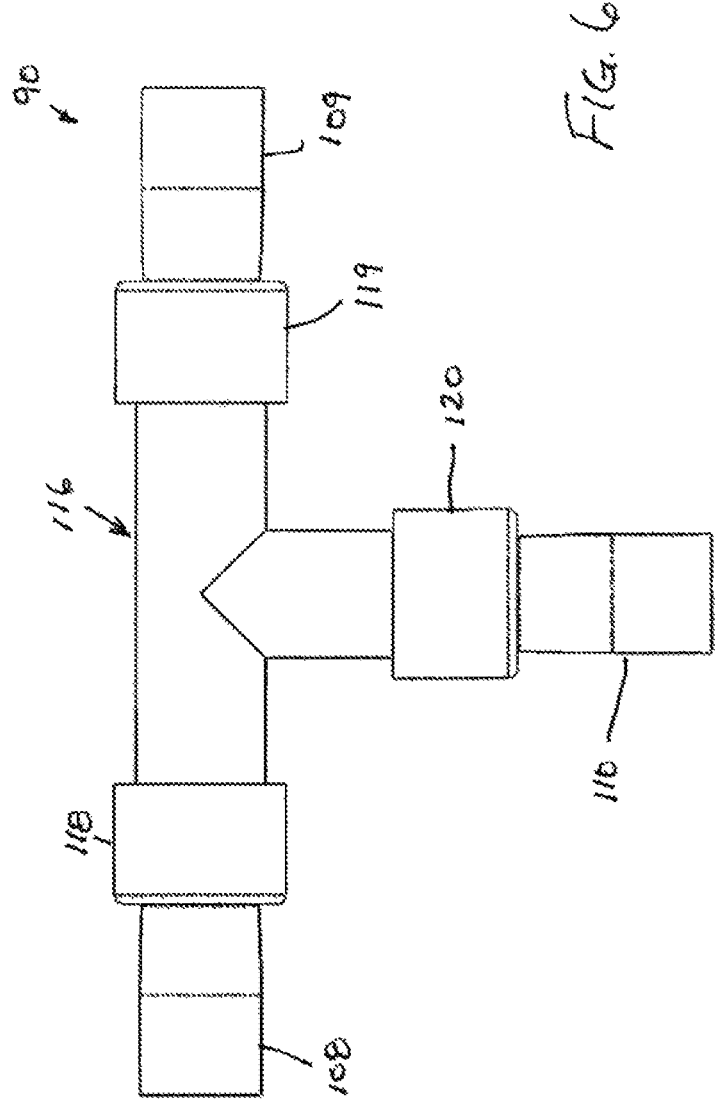
FIG. 6 is a side elevational view of the connector and tubing assembly of FIG. 5.

FIGS. 5 and 6 show a connector and tubing assembly 90 comprising a preformed connector member or joint fitting element 92 having a T configuration with three ends 94-96 with respective openings 97-99 that communicate with one another through a lumen 100 of the connector member. Connector member 92 is formed at each end 94-96 with a respective tapered annular ridge or conical projection 102-104 extending radially outwardly from an outer surface 106 of the connector member. Three tubes 108-110 each having a terminal portion 112-114 are coupled to connector member 92. Ends 94-96 of connector member 92 are each inserted into the terminal portion 112-114 of a respective tube 108-110 so that the respective terminal portion is deformed to flare outwardly, as shown in FIG. 5. A layer of thermoplastic or polymeric material is molded about the entirety of connector member 92 and concomitantly or inherently about the terminal portions 112-114 of tubes 108-110 so that the layer of thermoplastic or polymeric material is bonded to the connector member and the terminal tube portions to form a single T-shaped sleeve, shell or envelope 116 having enlarged end segments 118-120.

Connector and tubing assembly 90 is fabricated by inserting each of the ends 94-96 into a respective terminal portion 112-114 of tubes 108-110 so that the respective terminal portion 112-114 is deformed and flares outwardly. Subsequently the thermoplastic or polymeric material is molded about connector member 92 and about the terminal portions 112-114 of tubes 108-110 so that the thermoplastic or polymeric material is bonded to the connector member and the terminal portions.

Figure 7:
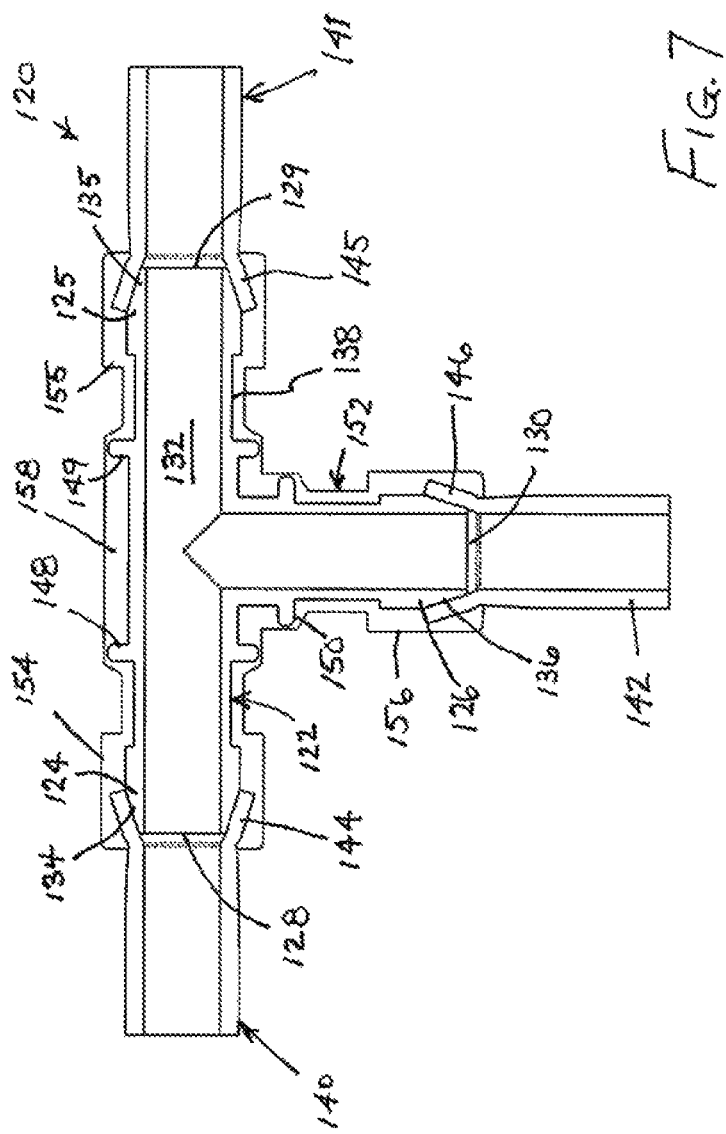
FIG. 7 is a cross-sectional view of an additional connector and tubing assembly or fluid-flow circuit joint pursuant to the present invention fabricated by a method in accordance with the invention.
Figure 8:
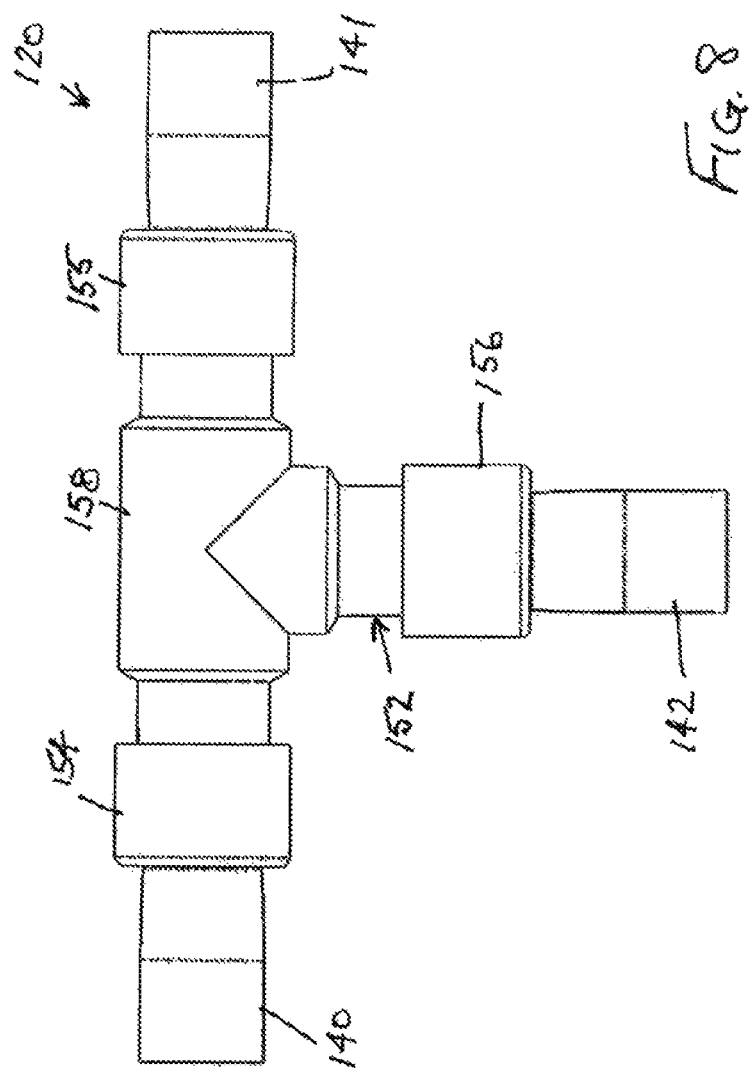
FIG. 8 is a side elevational view of the connector and tubing assembly of FIG. 3.

FIGS. 7 and 8 show another connector and tubing assembly 120 comprising a preformed connector member or joint fitting element 122 having a T configuration with three ends 124-126 with respective openings 128-130 that communicate with one another through a lumen 132 of the connector member. Connector member 122 is foamed at each end 124-126 with a respective tapered annular ridge or conical projection 134-136 extending radially outwardly from an outer surface 138 of the connector member. Three tubes 140-142 each having a terminal portion 144-146 are coupled to connector member 122. Ends 124-126 of connector member 122 are each inserted into the terminal portion 144-146 of a respective tube 140-142 so that the respective terminal portion is deformed to flare outwardly, as shown in FIG. 7. Connector member or fitting element 122 is further formed along outer surface 138 with three annular ribs or rings 148-150, one for each arm (not separately designated) of the T-shaped connector. A layer of thermoplastic or polymeric material is molded about the entirety of connector member 122, including ribs or rings 148 and 150 -and, concomitantly or inherently about the terminal portions 144-146 of tubes 140-142 so that the layer of thermoplastic or polymeric material is bonded to the connector member and the terminal tube portions to form a single T-shaped sleeve, shell or envelope 152 having enlarged end segments 154-156 and an enlarged T-shaped center piece 158.

Connector and tubing assembly 120 is fabricated by inserting each of the ends 124-126 into a respective terminal portion 144-146 of tubes 140-142 so that the respective terminal portion 144-146 is deformed and flares outwardly. Subsequently the thermoplastic or polymeric material is molded about connector member 122 and about the terminal portions 144-146 of tubes 140-142 so that the thermoplastic or polymeric material is bonded to the connector member and the terminal portions.

It is to be noted that the flaring of the terminal portions 144-146 serve in part to anchor tubes 140-142 to connector member 122 and provide an enhanced resistance or countervailing force in the event that a tensile force is applied to tubes 140-142 that would tend to pull them out of the sleeve or envelope 152. These advantages pertain also to the above-described embodiments of FIGS. 1-6.

Ribs or rings 148-150 can partially melt during the application of the thermoplastic resin material and thus provide an enhanced or stronger bonding of the connector 122 to the sleeve or envelope 152.

FIGS. 9 and 10 show another connector and tubing assembly 160 comprising a preformed connector member or fitting 162 incorporating a filter element 163 and having a linear configuration with two ends 164, 166 with respective openings 168, 170 that communicate with one another through a lumen 172 of the connector member. Connector or inline filter member 162 is formed at each end 164, 166 with a respective tapered annular ridge or conical projection 174, 176 extending radially outwardly from an outer surface 178 of the connector member. Two tubes 180, 182 each have a terminal portion 184, 186 provided along an inner surface 188, 190 of the respective tube 180, 182 with an annular recess or groove 192, 194 configured to =receive or seat a respective projection 174, 176. Preferably recesses 192, 194 and projections 174, 176 are geometrically similar to provide a snug fit of the projections into the corresponding recesses. Ends 164, 166 of connector member 162 are each inserted into the terminal portion 184, 186 of a respective tube 180, 182 so that the respective projection 174, 176 is seated in the respective recess 192, 194, as shown at 174, 192 in FIG. 10. Connector member or fitting element 162 is further formed along outer surface 178 with two pair of annular ribs or rings 196, 198. A layer of thermoplastic or polymeric material is molded in two spaced aliquots or masses 200 about ends of connector member 162, including ribs or rings 196 and 198 and, concomitantly or inherently about the terminal portions 184, 186 of tubes 180, 182 so that the masses 200 of thermoplastic or polymeric material are bonded to the connector member and the terminal tube portions to form the masses 200 as two sleeves (only one shown). Connector member 162 like other linear connectors or fittings shown herein is provided with a central flange 202 that contains and holds filter element 163. If flange 202 is formed at a junction between two separate connector halves, aa thermoplastic layer or sleeve 203 may be overmolded about the flange. (Likewise, flanges 25 and 55 of connector or inline filter members 22 and 52, when formed at a junction between two separate connector halves, are typically encased in overmolded thermoplastic sleeves that serve to sealingly couple the connector halves at the flange 25, 55.) Where the entire connector member 162 (or 22 or 52) including flange 202 (or 25 or 55) is provided with a singular or unitary overmolded shell or casing (as in FIGS. 5 and 6 and FIGS. 7 and 8), flange 202 is also enveloped by the shell or casing.

Connector and tubing assembly 160 is fabricated by inserting each of the ends 164, 166 into a respective terminal portion 184, 186 of tubes 180, 182 so that the projections 174, 176 are seated in respective recesses 192, 194. Subsequently the thermoplastic or polymeric material is molded about connector member 162 and about the terminal portions 144-146 of tubes 140-142 so that the thermoplastic or polymeric material is bonded to the connector member and the terminal portions.

It is to be noted that the mating of projections 174, 176 with recesses 192, 194 serve in part to anchor tubes 180, 182 to connector member 162 and provide an enhanced resistance or countervailing force in the event that a tensile force is applied to tubes 180, 182 that would tend to pull them out of the sleeves 200.

Ribs or rings 196, 198 partially melt during the application of the thermoplastic resin material, as indicated schematically by their partial forms in FIG. 10, and thus provide an enhanced or stronger bonding of the connector 162 to the sleeves 200.

As illustrated in FIG. 11, a connector and tubing assembly 210 comprises two preformed connector members or joint fitting elements 212, 214 each having a first end with a flange 216, 218 and a second end with a respective tapered annular ridge or conical projection 220, 222 extending outwardly from an outer surface 224, 226 of the respective connector or fitting member. Flanges 216 and 218 are placed in juxtaposition with one another and in direct or indirect contact, the latter being the case if a gasket or sealing ring (not shown) is interposed between the flanges 216, 218. Two tubes 228, 230 each have a terminal portion 232, 234 provided along an inner surface 236, 238 of the respective tube with an annular recess or groove 240, 242 configured to receive or seat a respective projection 220, 222. Preferably recesses 240, 242 and projections 220, 222 are geometrically similar to provide a snug fit of the projections into the corresponding recesses. The second ends of connector members 212, 214 are each inserted into the terminal portion 232, 234 of a respective tube 228, 230 so that the respective projection 220, 222 is seated in the respective recess 240, 242. A layer of thermoplastic or polymeric material is molded in two spaced aliquots or masses 244, 246 about the second ends of connector members 212, 214 and, concomitantly or inherently about the terminal portions 232, 234 of tubes 228, 230 so that the masses 244, 246 of thermoplastic or polymeric material are bonded to the respective connector members 212, 214 and the terminal tube portions 232, 234 to form the masses 244, 246 as two sleeves. A further aliquot or mass 248 of the thermoplastic or polymeric resin material is molded about juxtaposed flanges 216, 218 to form a third sleeve which binds and seals the connector members 212 and 214 to one another.

The fabrication of connector and tubing assembly 210 is the same as in other assemblies described herein except that the two connectors 212, 214 must be held in fixed relation to one another, with flanges 216, 218 in contact during the formation of molded sleeve 248.

As depicted in FIG. 12, the present methodology, not using any molding insert that must be removed from the joint after the overmolding process, enables the formation of tortuous paths. FIG. 12 shows a fluidic circuit assembly exhibiting a tortuous path in the form of a closed loop 250 wherein a tube 251 extends from connector or joint assembly 252 at an output 254 of a pump or mixer 256 to a connector or joint assembly 258 at an input 260 of the pump or mixer. Each joint assembly 252 and 258 is formed by the overmolding technique described herein wherein a connector member or fitting element 262, 264 remains in place after the formation of overmolded sleeves or joint masses 266, 268 of thermoplastic resin or polymer.

Figure 13:
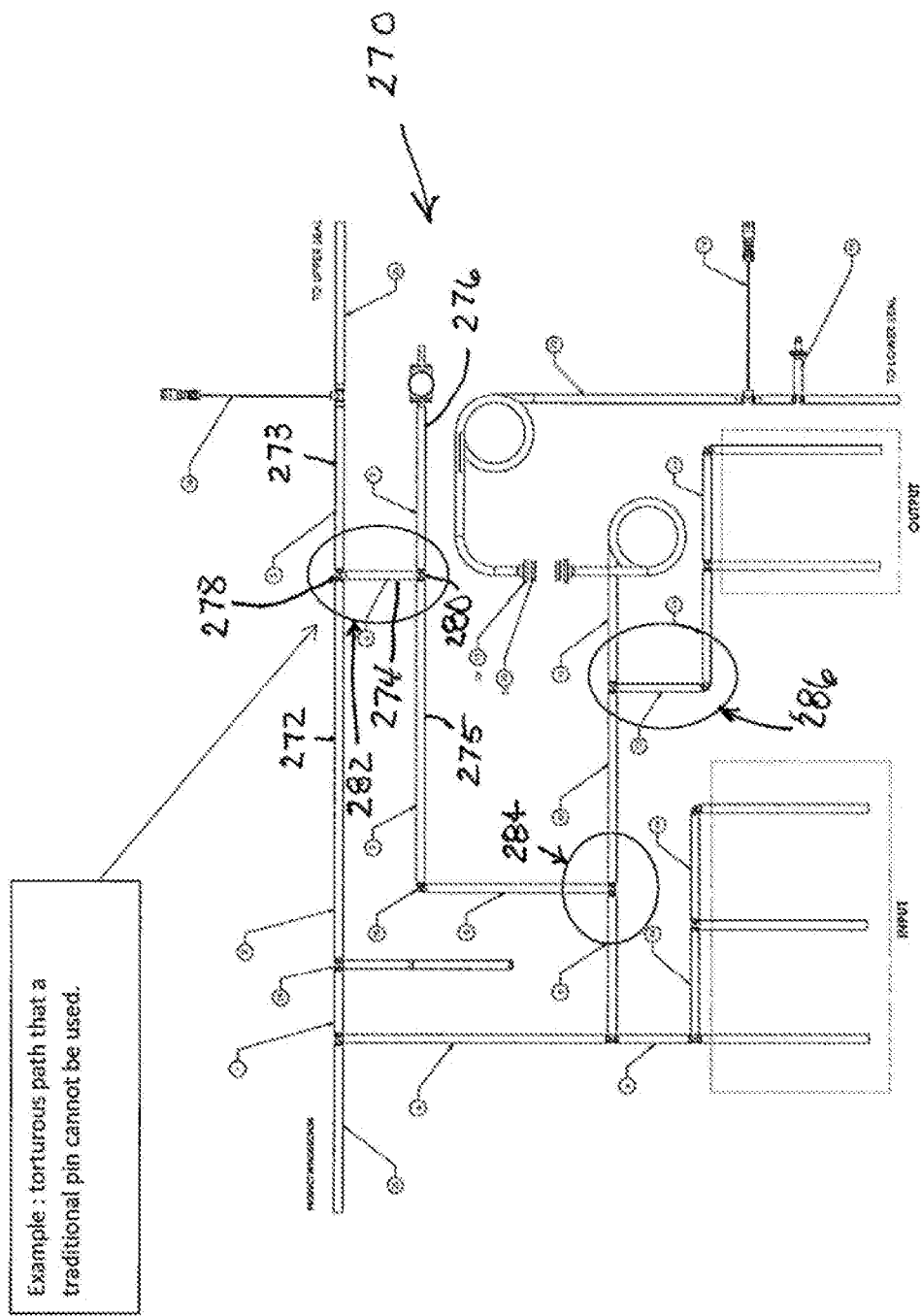
FIG. 13 is a diagrammatic view of a fluid-processing circuit, on a smaller scale, showing nonlinear or tortuous path segments, fabricated by a method pursuant to the invention.

FIG. 13 depicts another fluid-processing circuit 270 that can be easily fabricated owing to the overmolding method of the present invention, wherein any mold-forming component remains in place as part of the fluid processing circuit. Circuit 270 includes, among other circuit components, five tubes 272-276 that are connected one another at a pair of T-joints or couplings 278 and 280 that include respective three-pronged connectors or filltings (not separately labeled). It is to be noted that the five tubes 272-276 and two T-joints of couplings 278 and 280 form a nonlinear or tortuous fluid flow path 282. This path can be formed at both joints 278 and 280 even though tube 274, which extends between the joints or coupling 278 and 280 is necessarily closed or blocked during formation of at least one of the two joints or couplings 278 and 280. Accordingly, the respective connector member or fitting is not accessible via tube 274. Circuit 270 includes other such tortuous path segments 284 and 286.

As shown in FIG. 14, a connector and tubing assembly 290 formed by an overmolding method as described hereinabove comprises a manifold connector member or fitting 292 having a multiplicity of ends or ports 294 each communicating with the other ports via a housing or body 296. Connector or fitting 292 may be provided with meltable projections (not shown) and/or mating projections (not shown) on ports 294 for insertion into respective recesses (not shown) formed in the lumens of respective tubes 298, as discussed above, for instance, with reference to FIG. 11. Ports 294 may be inserted into terminal portions of respective tubes 298 so that the terminal portions flare outwardly as shown in FIGS. 1, 3, 5, and 7.

As illustrated in FIG. 15, a connector and tubing assembly 300 formed by an overmolding method as described hereinabove may comprise a plurality of connector members, fittings, and functional fluid-processing components 302 that are coupled to one another in a matrix, with connector ends being juxtaposed to one another and in direct o indirect contact as discussed above with reference to FIGS. 9 and 10. Some of the connector members, fittings, functional fluid-processing components 302 are coupled at one end 304 to respective tubes 306. Connectors or fittings 302 may be provided with meltable projections (not shown) and/or mating projections (not shown) proximate ends 304 for insertion into respective recesses (not shown) formed in the lumens of respective tubes 306, as discussed above exemplarily with reference to FIG. 11. Ends 304 may be inserted into terminal portions of respective tubes 306 so that the terminal portions flare outwardly as discussed above with reference to FIGS. 1, 3, 5, and 7, Connector members, fittings, and functional fluid-processing components 302, together with the terminal portions of tubes 306 are encased in a unitary block 308 of overmolded thermoplastic or polymeric material. Overmold casing block 308 may be a standard shell with blocks to block out portions.

FIG. 16 shows a connector and tubing assembly 310 formed by an overmolding method as described hereinabove, wherein two connector members or fittings 312 have open ends 314 that are juxtaposed to one another and in effective contact, direct or indirect. Connector members or fittings 312 have annular projections or ribs 316 (alternatively circumferentially spaced fingers or tbs) that are spaced from the juxtaposed ends 314 and that may be partially melted by thermoplastic material overmolded to form a sleeve of coupling element 318.

FIG. 17 shows a connector and tubing assembly 320 formed by an overmolding method as described hereinabove, wherein two connector members or fittings 322 have open ends 324 that are juxtaposed to one another and in effective contact, direct or indirect. Connector members or fittings 322 have conical or tapered annular projections or ribs 326 (alternatively circumferentially spaced fingers or tbs) that extend from the juxtaposed ends 324 and serve as anchors for the overmolded thermoplastic material 328.

It is to be understood that any of the structural elements disclosed herein may be used in any combination with the other structural elements to provide another specific embodiment of the invention. As indicated herein with reference to FIGS. 1-4, 9 and 10, a connector member in a tubing joint assembly may incorporate functional elements such as filters, pumping elements, diaphragms, etc., for performing dedicated functions in a fluid-flow circuit. The connector member can then be called by a functional name. However the housing or casing of the functional component serves as a connector to multiple tubes in the circuit as fabricated pursuant to the method taught herein

What is claimed is:

1. A method of molding a connector and tubing assembly comprising:
providing a connector member including a plurality of ends with respective openings that communicate with one another via a lumen of said connector member, said connector member having one or more projections extending outwardly from an outer surface;
inserting at least one of said ends into a terminal portion of a respective tube;
molding a layer of thermoplastic or polymeric material about at least a portion of said connector member and about said terminal portion; and
during the molding of said thermoplastic or polymeric material melting at least a portion of each of said one or more projections into the thermoplastic or polymeric material to enhance bonding of said connector member to said layer of thermoplastic or polymeric material.

2. The method defined in claim 1 wherein the molding of the layer of thermoplastic or polymeric material about said connector member and about said terminal portion includes applying said thermoplastic or polymeric material in separate aliquots to a plurality of terminal portions of respective tubes to form a plurality of spaced over-molded sleeves.

3. A method of molding a connector and tubing assembly comprising:
providing a connector member including a plurality of ends with respective openings that communicate with one another through a lumen of said connector member, said connector member being formed at at least one of said ends with a projecting structure extending radially outwardly from an outer surface of said connector member;

providing at least one tube having a terminal portion with a profiled inner surface having a recess configured to receive or seat the projecting structure of said at least one of said ends;

inserting said, at least one of said ends into a terminal portion of said at least one tube so that said projecting structure is received or seated in the respective recess; and subsequently molding a layer of thermoplastic or polymeric material about at least a portion of said connector member and about said terminal portion so that said thermoplastic or polymeric material is bonded to said connector member and said terminal portion.

4. The method defined in claim 3 wherein the molding of the layer of thermoplastic or polymeric material about said connector member and about said terminal portions includes applying said thermoplastic or polymeric material in separate aliquots at said terminal portions to form a plurality of spaced over-molded sleeves equal in number to said ends.

5. A method of molding a connector and tubing assembly comprising:

providing a plurality of connector members each including a plurality of ends with respective openings that communicate with one another through a lumen of the respective connector member, said connector members each being formed with a projecting structure extending outwardly from an outer surface of the respective connector member;

placing one end of each of said connector members in juxtaposition with an end of another one of said connector members so that said connector members communicate with one another and are in direct or indirect contact or engagement with one another at the juxtaposed ends of said connector members;

subsequently molding a layer of thermoplastic or polymeric material about at least a portion of each of said connector members including the juxtaposed ends of the connector members and the projecting structures so that said thermoplastic or polymeric material is bonded to said connector members at least in a region about the juxtaposed ends of the connector members and so that said layer of thermoplastic or polymeric material fixes said connector members to one another; and maintaining said juxtaposed ends of said connector members in direct or indirect contact with one another during the molding of said layer of thermoplastic or polymeric material.

6. The method defined in claim 5 wherein the molding of the layer of thermoplastic or polymeric material about said connector member and about said terminal portions includes applying said thermoplastic or polymeric material in separate aliquots at said terminal portions and at said contacting ends.

* * * * *